US00PP09523P

United States Patent [19]

Koppe

[11] Patent Number: Plant 9,523

[45] Date of Patent: Apr. 23, 1996

[54] BEGONIA PLANT NAMED 'BARKOS'

[75] Inventor: Lubbertus H. Koppe, AM Ermelo, Netherlands

[73] Assignee: M. Koppe B.V., Ermelo, Netherlands

[21] Appl. No.: 361,319

[22] Filed: Dec. 21, 1994

[51] Int. Cl.[6] ..... A01H 5/00

[52] U.S. Cl. ..... Plt./87.18

[58] Field of Search ..... Plt./87.17, 87.18

*Primary Examiner*—James R. Feyrer

*Attorney, Agent, or Firm*—Foley & Lardner

[57] ABSTRACT

A begonia plant named Barkos particularly characterized by flowering throughout the year, double-flowering with many rows of petals, red flower color, strong and thick stalks, compact habit, outstanding keeping quality through the winter and dark foliage.

3 Drawing Sheets

The present invention relates to a new and distinctive cultivar of begonia plant, botanically known as *Begonia hiemalis* Fotch and known by the cultivar name Barkos.

The new cultivar was discovered by L. H. Koppe in October 1988 in Ermelo, The Netherlands as a seedling from a controlled cross of a proprietary *Begonia tuberosa* selection (T-251253) as the seed parent with an unnamed non-proprietary selection of *Begonia socotrana* as the pollen parent.

The new cultivar was asexually propagated for the first time in May 1989 in Ermelo, The Netherlands. Asexual reproduction by leaf cuttings has reproduced the unique features of the new cultivar through successive propagations.

The following characteristics distinguish the new begonia from both its parents and other begonias commercially known and used in the floriculture industry:

1. The seed parent only flowers during long days whereas Barkos flowers throughout the year.
2. The pollen parent has a small single flower whereas Barkos is double-flowering.
3. Barkos is strongly double-flowering with many rows of petals.
4. Flower color of pollen parent is light pink whereas Barkos is red.
5. Compared to Azotus, the variety Barkos has stronger and thicker stalks.
6. Barkos is more compact than Azotus.
7. The keeping quality of Barkos is outstanding and keeps longer than any begonia variety currently known in the market.
8. Barkos keeps its flower color very well through the winter.

The accompanying color photographs were taken on Oct. 15, 1994 in s'-Gravenzande, The Netherlands and illustrate the overall appearance of this cultivar. FIG. 1 is an oblique view of the plant grown in a 13 cm plastic pot.

Figure 1:
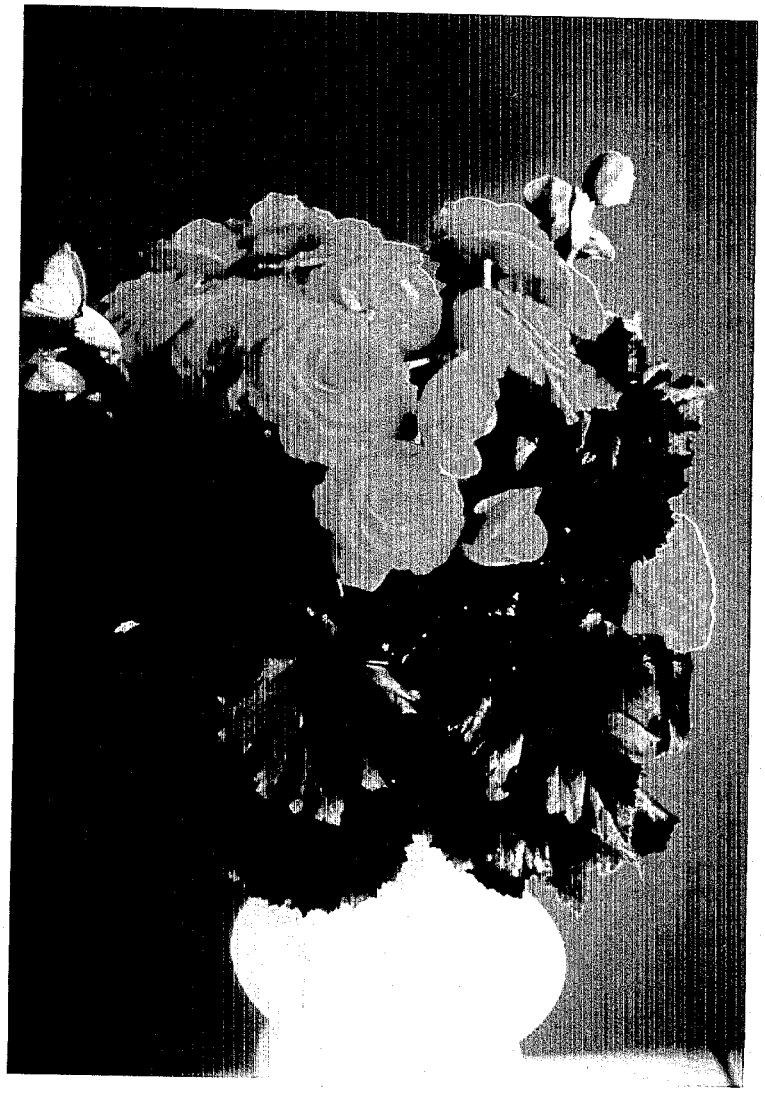
Figure 2:
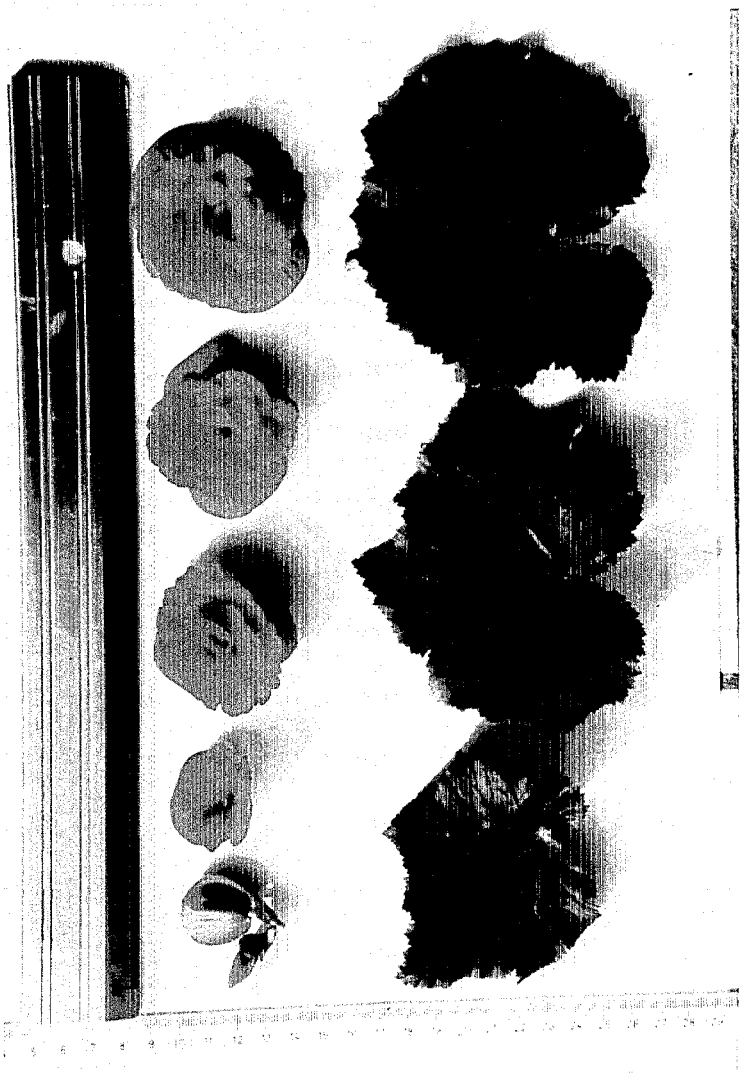
FIG. 2 shows the upperside of the flower and the leaves at different developmental stages.
Figure 3:
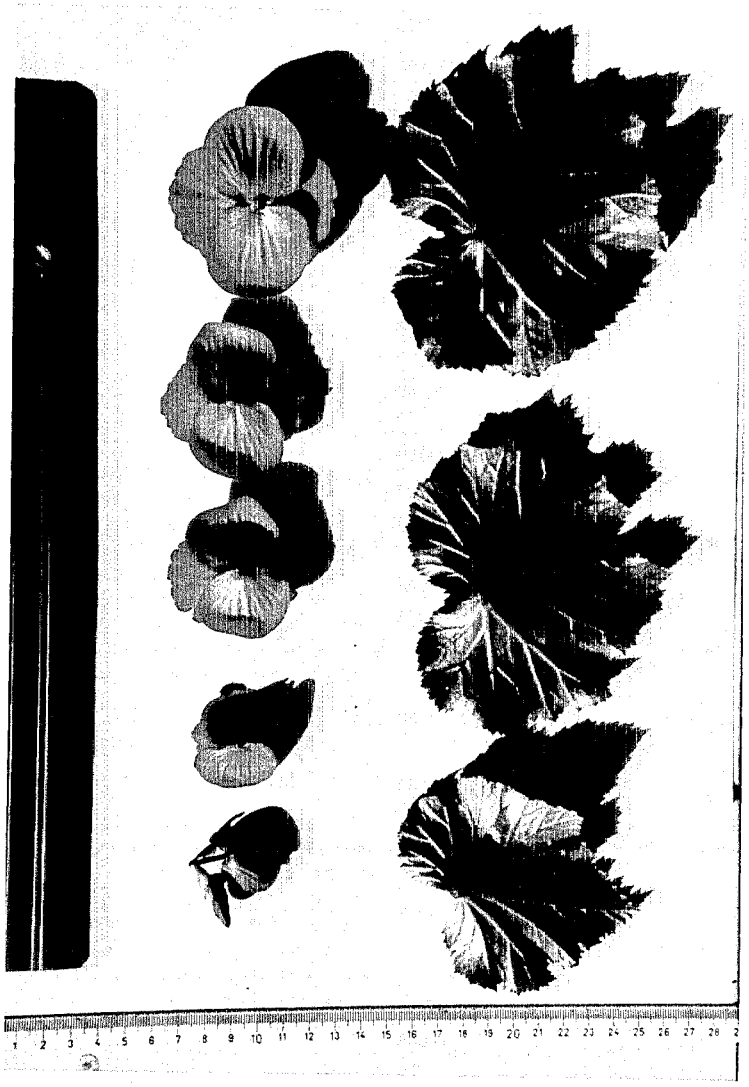
FIG. 3 shows the underside of the flower and leaves at different developmental stages. The colors in the photograph are as true as reasonably possible in a color reproduction of this type.

The new cultivar Barkos is principally distinguishable from other begonia varieties by its red double-type flowers and outstanding keeping quality. Asexual reproduction of the new cultivar Barkos as performed by applicant at Ermelo, The Netherlands has demonstrated that the combination of characteristics herein disclosed for the new cultivar are firmly fixed and returned through successive generations of asexual reproduction. Barkos has not been observed under all possible environmental conditions. The phenotype may vary with variations in environment such as temperature, light intensity and day length without a change in genotype.

The following is a detailed description of the new begonia cultivar based on plants produced under commercial practices in Ermelo, The Netherlands. Color references are made to The Royal Horticultural Society (R.H.S.) Colour Chart except where general terms of ordinary dictionary significance are used.

Parentage:

*Female parent.*—*Begonia tuberosa.*

*Male parent.*—*Begonia socotrana.*

Propagation:

*Type cutting.*—Top and/or leaf cutting.

*Time to root.*–5 weeks at 20°–25° C. summer; 5 weeks at 20°–25° C. winter.

*Rooting habit.*–Spreading.

*Time for shoot development.*–6–7 weeks after sticking by a top cutting, 7–8 weeks by leaf cutting.

Plant description:

*Form.*—Spreading.

*Habit of growth.*—Upright growth.

*Height.*—28 cm.

*Width.*—31 cm.

*Foliage.*—Dark green. Size: Juvenile leaf: Width 80 mm; length of midrib 72 mm. Half mature: Width 115 mm; length of midrib 78 mm. Mature: Width 120 mm; length of midrib 80 mm. Shape: Open to closed. Texture: Glabrous. Margin: Bi-serrate. Color (young foliage): Top side 147A/B; under side 148B/C. Color (mature foliage): Top side 147A; under side 148B. Veination: 148D.

Flowering description:

*Flowering habits.*—Floriferous with branched inflorescence.

*Natural flowering season.*—Mid-February until November.

*Flower bud description.*—Sepals are light green turning a little reddish to the tip.

*Flowers borne.*—From axillary buds.

*Quantity.*—7–9 flowers from one stem out of axillary bud.

*Tepals.*—Shape: Double flower. Color (top side in winter when opening): Outer flower petals 46B inner flower petal 44A, not fading. Color (underside in winter when opening): Outer petal 39A, inner petal 46C. Number: Up to 37 per flower. Size: Differ by petal and flower. Flower size: Diameter 63 mm, outer petal 70 mm, inner petal 53 mm.

The flowers do not have stamens or anthers. These structures are transformed into petals. Barkos does not have female reproductive organs.

Disease resistance: Unknown.

Other characteristics: Barkos is a very strong cultivar that produces good cuttings, roots well and exhibits excellent keeping quality including maintenance of red flower color. The root system of Barkos does not form tubers.

While Barkos has a propensity to form branches with or without pinching, pinches plants have a greater propensity to form branches. The internode length is about 3 cm.

What is claimed is:

1. A new and distinct begonia plant named Barkos, as described and illustrated.

* * * * *